(12) United States Patent
Nakagawa et al.

(10) Patent No.: US 11,464,196 B2
(45) Date of Patent: Oct. 11, 2022

(54) DOUBLE-FLOWERED PENTAS PLANT AND METHOD FOR GROWING SAME

(71) Applicant: SAKATA SEED CORPORATION, Yokohama (JP)

(72) Inventors: Masahiro Nakagawa, Yokohama (JP); Akihiro Torii, Yokohama (JP)

(73) Assignee: SAKATA SEED CORPORATION, Yokohama (JP)

( * ) Notice: Subject to any disclaimer, the term of this patent is extended or adjusted under 35 U.S.C. 154(b) by 6 days.

(21) Appl. No.: 16/956,862

(22) PCT Filed: May 17, 2018

(86) PCT No.: PCT/JP2018/019050
§ 371 (c)(1),
(2) Date: Jun. 22, 2020

(87) PCT Pub. No.: WO2019/220586
PCT Pub. Date: Nov. 21, 2019

(65) Prior Publication Data
US 2020/0323160 A1    Oct. 15, 2020

(51) Int. Cl.
*A01H 6/76* (2018.01)
*A01H 3/00* (2006.01)
*A01H 5/02* (2018.01)
*A01H 1/00* (2006.01)

(52) U.S. Cl.
CPC .............. *A01H 6/76* (2018.05); *A01H 1/1215* (2021.01); *A01H 3/00* (2013.01); *A01H 5/02* (2013.01)

(58) Field of Classification Search
CPC ....................................................... A01H 6/76
USPC .......................................................... Plt./466
See application file for complete search history.

(56) References Cited

U.S. PATENT DOCUMENTS

| PP19,409 | P2 * | 11/2008 | Nobuyuki ................ A01H 6/76 Plt./466 |
| PP19,410 | P2 * | 11/2008 | Nobuyuki ................ A01H 6/76 Plt./466 |
| PP19,544 | P2 | 12/2008 | Nobuyuki |

OTHER PUBLICATIONS

International Preliminary Report on Patentability, issued in PCT/JP2018/019050, dated Jun. 12, 2019.
International Search Report, issued in PCT/JP2018/019050, dated Aug. 14, 2018.
Tanaka et al., Registration Kind Database: "Raika Violet", [online]. Mar. 9, 2004 [retrieved: Jul. 3, 2018], Internet:<URL: hinshu2.maff.go.jp/vips/cmm/apCMM112.aspx?TOUROKU_NO=11873&LANGUAGE-Japanese>.
Tanaka, Registration Kind Database: "Raika Deep Pink", [online], Feb. 12, 2014, [retrieved: Jul. 3, 2018], Internet:<URL: hinshu2.maff.go.jp/vips/cmm/apCMM112.aspx?TOUROKU_NO=22999&LANGUAGE=Japanese>.
Tanaka, Registration Kind Database: "Raika Riv", [online], Feb. 12, 2014, [retrieved: Jul. 3, 2018], Internet:<URL: hinshu2.maff.go.jp/vips/cmm/apCMM112.aspx?TOUROKU_NO=22998&LANGUAGE=Japanese>.

(Continued)

*Primary Examiner* — David H Kruse
(74) *Attorney, Agent, or Firm* — Birch, Stewart, Kolasch & Birch, LLP

(57) ABSTRACT

A Pentas plant having a monogenic, incompletely dominant doubled-flower gene, a method for breeding the same, and a method for providing a Pentas variety with a doubled-flower or semi-double flower phenotype are provided for the purpose of creating a doubled-flower or semi-double flower Pentas plant with voluminous florets and a high ornamental value.

11 Claims, 3 Drawing Sheets

(56) References Cited

OTHER PUBLICATIONS

Watanabe, Registration Kind Database: "Princess Emi", [online], Mar. 25, 2002 [retrieved: Jul. 3, 2018], Internet: < URL: hinshu2.maff.go.jp/vips/cmm/apCMM112.aspx?TOUROKU_NO=10100&LANGUAGE=Japanese>.
Written Opinion of the International Searching Authority, issued in PCT/JP2018/019050, dated Aug. 14, 2018.

* cited by examiner

DOUBLE-FLOWERED PENTAS PLANT AND METHOD FOR GROWING SAME

This application is the U.S. National Phase of PCT/JP2018/019050 filed in Japan on May 17, 2018, the entire contents of all of which are expressly incorporated by reference into the present application.

TECHNICAL FIELD

The present invention relates to a Pentas plant having a doubled-flower gene.

BACKGROUND ART

Known ornamental varieties that continue to bloom during the summertime include crops such as Zinnia, Vince and Portulaca. But due to the effects of a recent abnormal warming climate, among other factors, new varieties with increased heat resistance are desired.

Pentas (Pentas Benth.) is a highly heat resistant plant in the Rubiaceae family that grows wild in tropical areas ranging from Eastern Africa to the south of the Arabian Peninsula. It has been reported that Pentas was brought into Europe in 1842 and a cultivated species (*Pentas lanceolate*) was bred. Pentas can be propagated from cuttings or seeds. Flowers of Pentas are terminal flowers, with about 20 to 60 florets arranged in a corymb ranging 6 to 10 cm in diameter. About 15 to 25 florets bloom simultaneously and form a hemispheric inflorescence. The florets are 5 lobed, star-shaped gamopetalous flowers, hence the origin of the genus name, with a diameter of about 1.5 cm, a length of 2 to 3 cm, and a tubular shape. Known flower colors include red, pink, white, and lavender. The flower forms are classified into single and double in the Japanese Ministry, Forestry and Fisheries publication 'Evaluation Guidelines for the Plant Variety Protection, Pentas' (Non Patent Literature 1), but the varieties that are registered in the category of double are actually semi-double (Non-Patent Literature 2, Non-Patent Literature 3).

CITATION LIST

Patent Literature

Patent Literature 1:
International Publication No. WO 2017/048547

Non Patent Literature

Non Patent Literature 1:
Homepage of Plant Variety Protection Office at Ministry of Agriculture, Forestry and Fisheries, Evaluation Guidelines, Pentas
www.hinshu2.maff.go.jp/info/sinsakijun/kijun/1464.pdf
Non Patent Literature 2:
Homepage of Plant Variety Protection Office at Ministry of Agriculture, Forestry and Fisheries, Registered Plant Variety Database, 'Raika Deep Pink', Registration No. 22999,
www.hinshu2.maff.go.jp/vips/cmm/apCMM112.aspx?TOUROKU NO=22999&LANGUAGE=Japanese
Non Patent Literature 3:
Homepage of Plant Variety Protection Office at Ministry of Agriculture, Forestry and Fisheries, Registered Plant Variety Database, 'Princess Emi', Registration No. 10100,
www.hinshu2.maff.go.jp/vips/cmm/apCMM112.aspx?TOUROKU NO=10100&LANGUAGE=Japanese

SUMMARY OF INVENTION

Technical Problem

While the conventionally known flower forms of Pentas are single and semi-double, in recent years single varieties have remained highly popular in the Pentas market while the popularity of semi-double varieties have not increased.

The reason these varieties have not increased in popularity is because the existing varieties classified as double possess only two whirls of petals, being substantially semi-double, and those varieties, while there are several of them, have not been used seriously for breeding. There are no known varieties having true doubled flowers with more petal volume per inflorescence.

Usually plant varieties with a doubled-flower form not only have high product values themselves, but also are useful as mother lines for breeding to provide doubled flowering. In particular, if the doubled flowering variety is of monogenic and dominant inheritance, the usefulness as a mother line for breeding is high because the trait can easily be transferred to progeny by crossing.

Solution to Problem

As a result of intensive studies to solve the above-mentioned problems, the present inventors have found that the conventional semi-double varieties (double-petal flowers) are of a recessive genetic trait. The inventors have made the discovery of a monogenic, incompletely dominant gene that makes Pentas with doubled-flowers (triple or more whirls of petals), different from conventional varieties, and a method for breeding doubled-flowered Pentas using doubled-flower Pentas having the gene. The present invention has been completed based on these findings.

Accordingly, the present invention provides the following [1] to [13].

[1] A Pentas plant having a doubled-flower gene.
[2] The Pentas plant according to [1], wherein the doubled-flower gene is a monogenic, incompletely dominant gene.
[3] The Pentas plant according to [1] or [2], wherein the doubled-flower gene is a gene of the Pentas identified by the accession number FERM BP-22361.
[4] The Pentas plant according to any of [1] to [3], wherein the Pentas plant is homozygous for the doubled-flower gene.
[5] The Pentas plant according to [4], wherein the Pentas plant exhibits a doubled-flower phenotype.
[6] The Pentas plant according to any of [1] to [3], wherein the Pentas plant is heterozygous for the doubled-flower gene.
[7] The Pentas plant according to [6], wherein the Pentas plant exhibits a semi-double flower phenotype.
[8] The Pentas plant according to any of [1] to [7], wherein the Pentas plant is a seedling.
[9] The Pentas plant according to any of [1] to [7], wherein the Pentas plant is a clone.
[10] A plant body or a part of the plant body of the Pentas plant according to any of [1] to [9].
[11] The plant body or the part of the plant body of the Pentas plant according to [10], wherein the part of the plant body of the Pentas plant is a leaf, pollen, an embryo, a seed leaf, an embryonic axis, a meristematic cell, an ovule, a seed, a cell, a root, a root apex, a pistil, a stamen anther, a flower, or a stem.

[12] A method for breeding a Pentas plant having a doubled-flower gene, comprising the following steps (1) and (2):
(1) artificially crossing the Pentas plant according to any of [1] to [9] with an arbitrary Pentas plant; and
(2) selecting a Pentas plant having a doubled-flower gene from Pentas plants obtained by artificial crossing of step (1).
[13] A method for providing a Pentas variety with a doubled-flower or semi-double flower phenotype, comprising the following steps (1) to (4):
(1) artificially crossing the Pentas plant according to any of [1] to [9] with a Pentas variety to be provided with a doubled-flower or semi-double flower phenotype;
(2) selecting a Pentas plant having a doubled-flower gene from Pentas plants obtained by artificial crossing of step (1);
(3) artificially crossing a Pentas plant obtained by selection of step (2) or (4) with the Pentas variety used in step (1); and
(4) selecting a Pentas plant having a doubled-flower gene from Pentas plants obtained by artificial crossing of step (3), wherein steps (3) and (4) are conducted several times.

Advantageous Effects of Invention

The use of a Pentas plant having a novel doubled-flower gene provided by the present invention in breeding makes it possible to create a stable Pentas plant having the novel doubled-flower gene, which has not been conventionally known, with voluminous petals and a high ornamental value.

DESCRIPTION OF EMBODIMENTS

Figure 1:
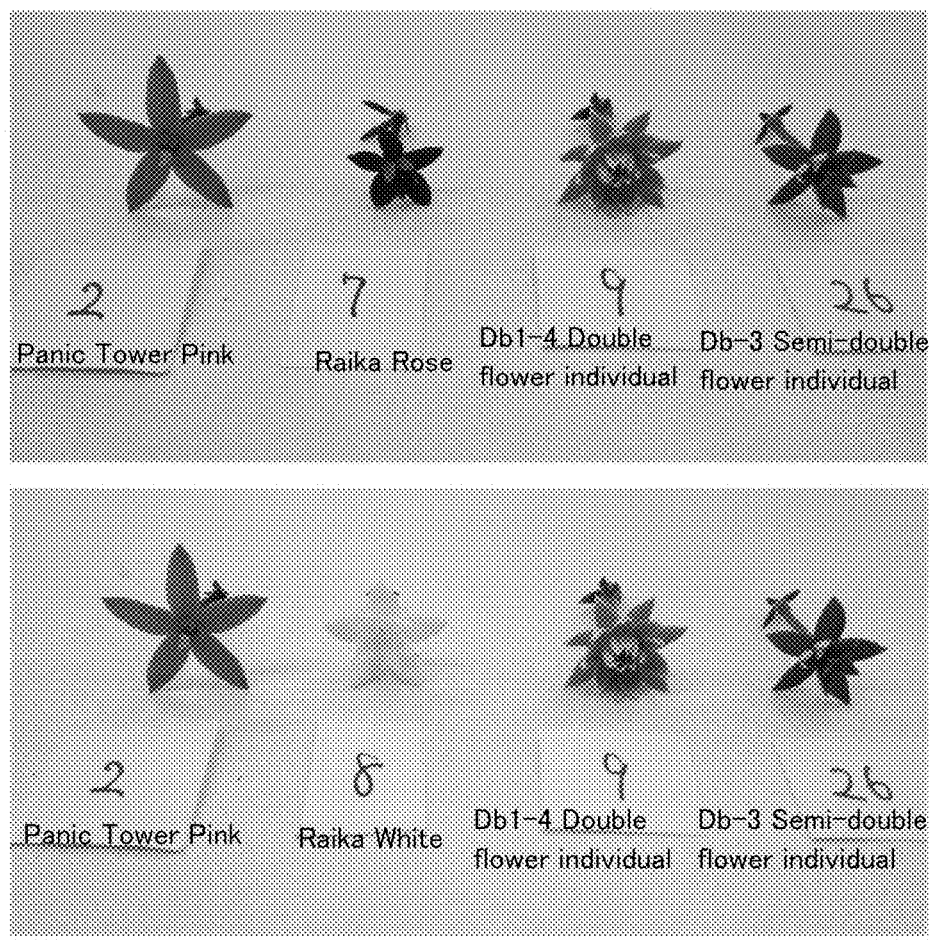
FIG. 1 is a set of photographs illustrating the morphology of florets of Pentas plants according to the present invention and commercially available Pentas varieties. From the left in the upper panel, 'Panic Tower Pink' (a commercially available variety), 'Raika Rose' (a commercially available variety), Db1-4 (a doubled-flower individual), and Db-3 (a semi-double flower individual) are shown. From the left in the lower panel, 'Panic Tower Pink', 'Raika White', Db1-4 (a doubled-flower individual), and Db-3 (a semi-double flower individual) are shown.

In the present invention, "Pentas plant" means a plant in the genus Pentas (Pentas Benth.).

In the present invention, flowers of Pentas plants are indeterminate with 20 to 60 florets arranged as a corymb ranging 6 to 10 cm in diameter. About 15 to 25 florets bloom simultaneously and form a hemispheric inflorescence. The terms "flower" or "flowers" according to the present invention means, unless otherwise specified, not the hemispheric inflorescence as a whole, but individual "florets" composing the inflorescence.

The florets of the Pentas plant according to the present invention are 5 lobed, star-shaped gamopetalous flowers, hence the origin of the genus name, with a diameter of about 1.5 cm, a length of 2 to 3 cm, and a tubular shape. There are those with long-styled flowers and those with short-styled flowers. Known flower colors include red, pink, white, and lavender.

In the present invention, "doubled" refers to 3 or more whirls of petals, which is also referred to as full-double. Since flowers of Pentas are gamopetalous flowers, the petals are fused to form one tubular petal. Accordingly, "3 or more whirls of petals" means 3 or more fused tubular petals.

In the present invention, "doubled-flower" refers to flowering in the state of petals being doubled.

In the present invention, "semi-double" refers to more than one and two or less whirls of petals, that is, 2 whirls of petals.

In the present invention, "semi-double flower" refers to flowering in the state of petals being semi-double.

In the present invention, "doubled-flower gene" means a gene that can cause a doubled-flower phenotype in Pentas.

In the present invention, "seedling" refers to a plant body obtained by a seed propagation method involving seeding a seed of a parental strain to sexually propagate a plant.

In the present invention, "clone" refers to a plant body having an identical genotype obtained by a vegetative propagation method involving asexually proliferating a part of the plant body of a parental strain.

In the present invention, "artificial crossing" means artificially crossing a pollen parent and a seed parent and refers, for example, to artificially collecting pollen from a pollen parent and artificially applying the pollen to stigmas of a seed parent.

(A) Pentas Plant Having Doubled-Flower Gene

The Pentas plant according to the present invention is a Pentas plant characterized by having a doubled-flower gene.

Variety SSC-PEN-18-001 comprising the doubled-flower gene whose seeds were deposited and accepted under the terms of the Budapest Treaty as follows (sometimes hereinafter referred to as "deposited doubled-flower gene").
Depository: National Institute of Technology and Evaluation (Independent Administrative Institution) Patent Microorganisms Depositary (Room No. 120, 2-5-8 Kazusakamatari, Kisarazu-shi, Chiba, Japan)
Accession number: FERM BP-22361
Accession date: Mar. 16, 2018
Type of deposition: International deposition This deposited doubled-flower gene is a monogenic, incompletely dominant gene and individuals that are homozygous for the doubled-flower gene exhibit a doubled-flower phenotype and individuals that are heterozygous for the doubled-flower gene exhibit a semi-double flower phenotype.

The Pentas plant according to the present invention has a doubled-flower or semi-double flower trait, and other traits (for example, the plant height, the size of corolla, the shape of corolla lobe, and the flower color) are not particularly limited. Known flower colors of Pentas include red, pink, white, and lavender, but the flower color of the Pentas plant according to the present invention may be any of these flower colors or a flower color other than these flower colors.

The Pentas plant according to the present invention includes not only the plant body of the Pentas plant, but also a part of the plant body of the Pentas plant. Examples of the part of the plant body include an organ, a tissue, a cell, a propagule, and a callus. Examples of the organ include a flower, a leaf, a stem, a root, and a seed. Examples of the tissue and cell include a tissue and a cell constituting a flower, a leaf, a stem, a root, or a seed, and specific examples thereof include pollen, an embryo, a seed leaf, an embryonic axe, a meristematic cell, an ovule, a root apex, a pistil, and stamen anther. Examples of a preferred part of the plant body of the Pentas plant include a leaf, a pollen, an embryo, a seed leaf, an embryonic axis, a meristematic cell, an ovule, a seed, a cell, a root, a root apex, a pistil, a stamen anther, a flower, or a stem.

(B) Method for Breeding Pentas Plant Having a Doubled-Flower Gene

The method for breeding a Pentas plant having a doubled-flower gene according to the present invention comprises the following steps (1) and (2):
(1) artificially crossing the Pentas plant having a doubled-flower gene with an arbitrary Pentas plant; and
(2) selecting a Pentas plant having a doubled-flower gene from Pentas plants obtained by artificial crossing of step (1).

The Pentas plant having a doubled-flower gene to be used is not particularly limited, either a Pentas plant that is homozygous for a doubled-flower gene or a Pentas plant that is heterozygous for a doubled-flower gene may be used. It is advantageous to use a Pentas plant that is homozygous for a doubled-flower gene because, theoretically, all individuals obtained by artificial crossing will have the doubled-flower gene, making selection easy. Meanwhile, use of a Pentas plant that is heterozygous for a doubled-flower gene is also advantageous in that artificial crossing is easy. This is because Pentas plants that are homozygous for a doubled-flower gene are often found to have abnormality in a reproductive organ such as a stamen or a pistil, but such abnormality is often absent or mild in Pentas plants that are heterozygous for a double flower gene.

An existing Pentas variety or the like may be used as the arbitrary Pentas plant. Moreover, Pentas plants having a doubled-flower gene may be crossed artificially as the arbitrary Pentas plants.

The artificial crossing may be performed according to a routine method.

The selection of the Pentas plant having a doubled-flower gene may also be performed according to a routine method. Since the deposited doubled-flower gene is an incompletely dominant gene, the phenotype of this gene is exhibited. Therefore, the selection can be carried out based on the phenotype (doubled-flower or semi-double flower).

(C) Method for Providing Doubled-Flower or Semi-Double Flower Phenotype to Pentas Variety The method for providing a Pentas variety according to the present invention with a doubled-flower or semi-double flower phenotype, comprising the following steps (1) to (4):
(1) artificially crossing the Pentas plant having a doubled-flower gene with a Pentas variety to be provided with a doubled-flower or semi-double flower phenotype;
(2) selecting a Pentas plant having a doubled-flower gene from Pentas plants obtained by artificial crossing of step (1);
(3) artificially crossing a Pentas plant obtained by selection of step (2) or (4) with the Pentas variety used in step (1); and
(4) selecting a Pentas plant having a doubled-flower gene from Pentas plants obtained by artificial crossing of step (3), wherein steps (3) and (4) are conducted several times.

The Pentas variety to be used is not particularly limited, and a variety whose product value would be increased by being provided with a doubled-flower or semi-double flower phenotype is preferably used.

The Pentas plant having a doubled-flower gene to be used may be a Pentas plant that is the same as in the above "Method for breeding Pentas plant having doubled-flower gene", the artificial crossing and the selection may also be carried out in the same way.

The number of times carrying out steps (3) and (4) may be the same as the number of times of usual continuous backcross and may be, for example, about 2 to 8 times.

EXAMPLES

The present invention will be described in more detail with reference to Examples. The present invention is not limited to these Examples, but encompasses the scope of the claims and the scope equivalent to the scope of the claims.

Example 1 (Breeding of Semi-Double Strains)

In this Example, a Pentas strain exhibiting doubled flowers having a relatively large number of petals and strains in the inventor's possession were crossed to create a large number of strains. From these, individuals exhibiting doubled flowers having 3 or more whirls of petals were selected, and the doubled trait of the progeny thereof was investigated.

In 2004, a producer of flower bed seedlings in Kobe-shi, Hyogo, Japan, found, an individual, from the commercially available Pentas variety 'New Look Rose', having doubled (semi-double) blooms and named it Individual 04K0-1. By 2007, F1 seeds of 5 strains were successfully obtained by crossing of Individual 04K0-1 and 5 commercially available varieties with different flower colors as set forth in Table 1. In December 2007, 5 individuals, resulting from seeding of the obtained F1 seeds, exhibiting the semi-double trait were confirmed and selected from the respective progeny. The strains were respectively named Db-1, Db-2, Db-3, Db-4, and Db-5 and F2 seeds were collected.

Example 2 (Breeding of Strains of the Present Invention and Comparison of Double Trait Thereof with Conventional Trait)

Subsequent seeding of the F2 seeds of the 5 Db strains yielded individuals, in each population, exhibiting doubled flowers having relatively large numbers of petals. Therefore, by 2011, 10 individuals were selected, respectively named Db-1a, Db-2a, Db-3a, Db-3b, Db-3c, Db-4a, Db-4b, Db-5a, Db-5b, and Db-5c, and preserved as clonal strains (Table 1).

TABLE 1

Breeding process of Strains Db

| Combination No. | Strain name | Female origin | Male origin | Range of flower color of progeny | Name of double individual selected from F2 |
|---|---|---|---|---|---|
| 2007-1 | Db-1 | 04K0-1 | × Shonan Kometto Pink | Rose to Pale pink | Db-1a |
| 2007-2 | Db-2 | 04K0-1 | × Shonan Kometto Purple | Rose to Pale pink | Db-2a |
| 2007-3 | Db-3 | 04K0-1 | × New Look Red | Rose | Db-3a, Db-3b, Db-3c |
| 2007-4 | Db-4 | 04K0-1 | × New Look White | Pale pink | Db-4a, Db-4b |
| 2007-5 | Db-5 | 04K0-1 | × New Look Pink | Rose to Pink | Db-5a, Db-5b, Db-5c |

In 2012, crossing was carried out by using the selected doubled individuals and the possessed single strains, as shown in Table 2. More specifically Sg-1 having a red flower color, Sg-2 having a pink flower color, and Sg-3 having a white flower color were crossed and progeny seeds were successfully obtained in all combinations. Moreover, crossing of existing doubled varieties (Raika strains) and single strains was carried out simultaneously to successfully obtain progeny seeds in 3 combinations. As a result, out of all examined individuals in the progeny, 3 of the 10 selected individuals, that is, Db-2a, Db-3a, and Db-5a were semi-double, as set forth in Table 2, while the remaining 7 individuals were segregated into single and semi-double. Meanwhile, all individuals in the progeny obtained from crossing 3 combinations of the Raika strains and the single strains Sg-1 and Sg-3 were examined and found to be single.

Based on this, it was concluded that the doubled-flower trait derived from Individual 04K0-1 was dominant and 3 individuals, Db-2a, Db-3a, and Db-5a, whose progeny was all doubled, were homozygous for the doubled-flower gene and the remaining 7 individuals were heterozygous. Meanwhile, it was concluded that the semi-double flower trait of the Raika strains was recessive and that the gene derived from Individual 04K0-1 was a novel doubled-flower gene, different from the known gene from the Raika strains.

Example 3 (Inheritance Pattern of Doubled Trait in Strains of Present Invention)

Over the period from 2015 to 2016, individuals of Db1-17 and Db1-5, which exhibit the semi-double trait, among Db1 strains were crossed to obtain seeds. In 2017, progeny seeds were seeded and then categorized into doubled (3 or more), semi-double (2), and single (1). Listed in Table 3 below are the numbers of individuals in each category, resulting in a ratio of approximately 1:2:1.

TABLE 2

Breeding process of Strains Db1 and result of crossing with single strains

| Combination No. | Strain name | Female origin | Male origin | Range of flower color of progeny | Number of investigated individuals | Semi-double | Single | Proportion of semi-double |
|---|---|---|---|---|---|---|---|---|
| 2012-1 | Db1-1 | Db-1a | × Sg-3 | Pale pink | 5 | 2 | 3 | 40% |
| 2012-3 | Db1-3 | Db-2a | × Sg-3 | Pale pink to White | 14 | 14 | 0 | 100% |
| 2012-4 | Db1-4 | Db-2a | × Sg-2 | Pale pink to White | 10 | 10 | 0 | 100% |
| 2012-5 | Db1-5 | Db-2a | × Sg-1 | Red to White | 13 | 13 | 0 | 100% |
| 2012-6 | Db1-6 | Db-3a | × Sg-3 | Pale pink | 15 | 15 | 0 | 100% |
| 2012-7 | Db1-7 | Db-3a | × Sg-2 | Rose to Pale pink | 12 | 12 | 0 | 100% |
| 2012-8 | Db1-8 | Db-3a | × Sg-1 | Red to Pale pink | 15 | 15 | 0 | 100% |
| 2012-9 | Db1-9 | Db-3b | × Sg-3 | Rose to Pale pink | 15 | 7 | 8 | 47% |
| 2012-10 | Db1-10 | Db-3b | × Sg-2 | Rose to Pale pink | 12 | 6 | 6 | 50% |
| 2012-11 | Db1-11 | Db-3c | × Sg-3 | Pale pink | 15 | 9 | 6 | 60% |
| 2012-12 | Db1-12 | Db-3c | × Sg-2 | Pale pink | 15 | 7 | 8 | 47% |
| 2012-13 | Db1-13 | Db-3c | × Sg-1 | Rose | 15 | 4 | 11 | 27% |
| 2012-14 | Dn1-14 | Db-4a | × Sg-3 | Pale pink to White | 15 | 3 | 12 | 20% |
| 2012-15 | Db1-15 | Db-4b | × Sg-3 | Pale pink to White | 15 | 10 | 5 | 67% |
| 2012-16 | Db1-16 | Db-5a | × Sg-2 | Rose to Pale pink | 14 | 14 | 0 | 100% |
| 2012-17 | Db1-17 | Db-5a | × Sg-1 | Red to Pink | 14 | 14 | 0 | 100% |
| 2012-18 | Db1-18 | Db-5b | × Sg-2 | Pale pink | 13 | 8 | 5 | 62% |
| 2012-19 | Db1-19 | Db-5c | × Sg-2 | Pale pink | 8 | 4 | 4 | 50% |
| 2012-21 | Db1-21 | Raika Small Pink | × Sg-1 | Red to Pale pink | 13 | 0 | 13 | 0% |
| 2012-22 | — | Raika White | × Sg-1 | | — | — | — | — |
| 2012-23 | Db1-23 | Raika Purple | × Sg-1 | Red, Purple | 10 | 0 | 10 | 0% |
| 2012-24 | — | Raika Blue | × Sg-1 | | — | — | — | — |
| 2012-25 | Db1-25 | Raika Red | × Sg-3 | Pale pink to White | 15 | 0 | 15 | 0% |
| 2012-26 | — | Raika White | × Sg-3 | | — | — | — | — |
| 2012-27 | — | Raika Purple | × Sg-3 | | — | — | — | — |
| 2012-28 | — | Raika Blue | × Sg-3 | | — | — | — | — |

"—" in the table indicates that no normal seeds were obtained and that the investigation was not possible.

TABLE 3

Result of crossing between semi-double individuals

| Combination No. | Female origin | Male origin | Range of flower color | Number of investigated individuals | Double | Semi-double | Single |
|---|---|---|---|---|---|---|---|
| 2017-127 | Db1-17 | × Db1-5 | Red to Rose | 320 (1.00) | 75 (0.23) | 166 (0.52) | 79 (0.25) |

The numerical values in ( ) indicate proportions.

From this result, it was concluded that the newly discovered doubled-flower gene has characteristics of being monogenic and incompletely dominant. Meaning, being homozygous for the gene results in full-double, that is, doubled with 3 or more whirls of petals, and being heterozygous for the gene results in semi-double, that is, 2 whirls of petals.

Example 4 (Creation of Plurality of Flower Color Strains Using Trait of the Present Invention)

Db strains, bred in 2007, had a range of flower colors from rose to pale pink (Table 1). In the progeny of Db1 strains created in 2012, namely Db1-5, Db1-8, and Db1-17 derived from red flowered Sg-1, segregation to semi-double flower individuals having a red flower color and other flower colors and single flower individuals was observed. Also in the progeny of Db1 strains created in 2012, namely Db1-3, Db1-14, and Db1-15 derived from white flowered Sg-3, s segregation to semi-double flower individuals having a white flower color to a pale pink flower color and single-petaled flower individuals was observed (Table 2). From this, it is concluded that the newly discovered doubled-flower gene is a trait that is inherited independently from flower color and creation of full-double flower or semi-double flower individuals having any flower color such as red, rose, pink, or white is possible by using this gene.

When the conventional existing recessive gene is used, only the semi-double trait can be created and breeding thereof requires the selection of individuals homozygous for the gene. Therefore, the range of combined strains is difficult to widen and, over a long period of time, will require much labor. However, by using the novel, incompletely dominant gene according to the present invention, the doubled-flower trait can be efficiently created. Furthermore, it is anticipated that it would become possible to efficiently create F1 hybrid varieties in a wide range of combinations having the semi-double trait by making them heterozygous for the gene.

Example 5 (Breeding of Clonal Variety Using Trait of the Present Invention)

Figure 2:
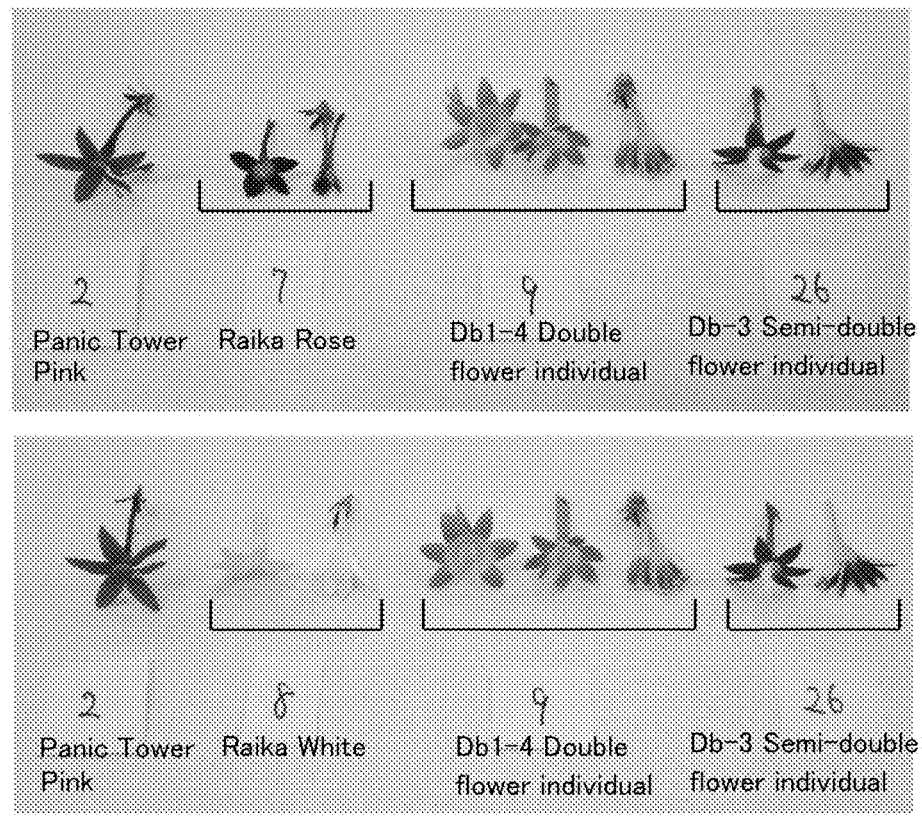
FIG. 2 is a set of photographs illustrating the morphology of dismantled florets of Pentas plants according to the present invention and commercially available Pentas varieties. From the left in the upper panel, 'Panic Tower Pink' (a commercially available variety), Raika Rose' (a commercially available variety), Db1-4 (a doubled-flower individual), and Db-3 (a semi-double flower individual) are shown. From the left in the lower panel, 'Panic Tower Pink' (a commercially available variety), 'Raika White' (a commercially available variety), Db1-4 (a doubled-flower individual), and Db-3 (a semi-double flower individual) are shown.
Figure 3:
FIG. 3 is a set of photographs illustrating the morphology of inflorescences (floret clusters) of Pentas plants according to the present invention and commercially available Pentas varieties. From the left in the upper panel, 'Panic Tower Pink' (a commercially available variety), 'Raika Rose' (a commercially available variety), Db1-4 (a doubled-flower individual), and Db-3 (a semi-double flower individual) are shown. From the left in the lower panel, 'Panic Tower Pink' (a commercially available variety), 'Raika White' (a commercially available variety), Db1-4 (a doubled-flower individual), and Db-3 (a semi-double flower individual) are shown.
Figure 3:
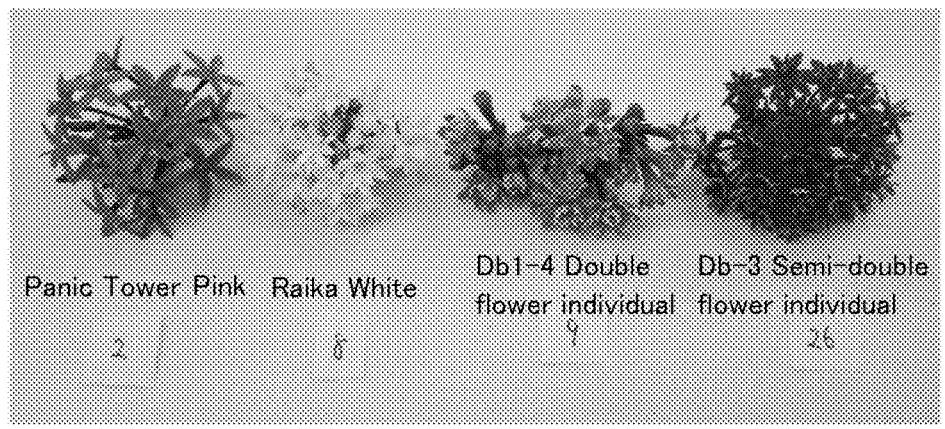

In 2015, self-fertilized seeds of each semi-double flower individual of the strains Db1-3, Db1-4, Db1-5, Db1-6, Db1-7, Db1-8, Db1-16, and Db1-17 were collected and the F2 generation for each strain was seeded. The segregation of various individuals having a range of flower colors shown in FIG. 2 and the flower forms of single, semi-double, and double was then observed. Accordingly, in total 12 individuals having the trait of the flower form of full-double flower and good plant shapes and flowering habits were selected and preserved as clonal strains. In 2017, the preserved individuals were propagated by cuttings obtained by rooting and growing in the same way as those of usual Pentas. The obtained rooted cuttings were naturalized in 10.5 cm pots, evaluated for their branching habit, internodal elongation, flowering habit, and the like, and then transplanted to an open field where their growth was examined. As a result, 2 individuals having dark pink and white flower colors exhibited particularly excellent flowering habit in pots and open field and, therefore, the variety breeding was judged to be completed for these varieties. The first clonal Pentas variety having a flower form of full-double flower has thereby been bred successfully.

All publications, patents, and patent applications cited herein are incorporated herein by reference as they are.

INDUSTRIAL APPLICABILITY

With voluminous florets, the Pentas plants according to the present invention have a high ornamental value. Moreover, the Pentas plants according to the present invention are useful as mother lines for breeding since the heredity of the doubled trait is monogenic and incompletely dominant and the trait can easily be transferred to progeny. Therefore, the Pentas plants according to the present invention are available in various gardening-related industrial fields including the seed industry.

The invention claimed is:

1. A Pentas plant comprising a monogenic incompletely dominant double flower gene that depending upon the zygosity of the double flower gene exhibits a semi-double or double flower phenotype, wherein the double flower gene provides 3 or more whirls of petals, and wherein the double flower gene is as found in variety SSC-PEN-18-001, a representative sample of seed comprising said double flower gene containing variety having been deposited under the accession number FERM BP-22361.

2. The Pentas plant according to claim 1, wherein the Pentas plant is homozygous for the double flower gene.

3. The Pentas plant according to claim 2, wherein the Pentas plant exhibits a double flower phenotype.

4. The Pentas plant according to claim 1, wherein the Pentas plant is heterozygous for the double flower gene.

5. The Pentas plant according to claim 4, wherein the Pentas plant exhibits a semi-double flower phenotype.

6. The Pentas plant according to claim 1, wherein the Pentas plant is a seedling.

7. The Pentas plant according to claim 1, wherein the Pentas plant is a clone.

8. A plant body or a part of the plant body of the Pentas plant according to claim 1.

9. The plant body or the part of the plant body of the Pentas plant according to claim 8, wherein the part of the plant body of the Pentas plant is a leaf, pollen, an embryo, a seed leaf, an embryonic axis, a meristematic cell, an ovule, a seed, a cell, a root, a root apex, a pistil, a stamen anther, a flower, or a stem, and has the double flower gene.

10. A method for breeding a Pentas plant having a double flower gene, comprising the following steps (1) and (2):
   (1) artificially crossing the Pentas plant according to claim 1 with a second Pentas plant; and (2) selecting a progeny Pentas plant having a double flower gene from Pentas plants obtained by artificial crossing of step (1).

11. A method for providing a Pentas variety with a double flower or semi-double flower phenotype, comprising the following steps (1) to (4):
   (1) artificially crossing the Pentas plant according to claim 1 with a second Pentas variety;
   (2) selecting a progeny Pentas plant having a double flower or semi-double flower phenotype from Pentas plants obtained by artificial crossing of step (1);
   (3) artificially back-crossing the progeny Pentas plant obtained by selection of step (2) with the second Pentas variety used in step (1);
   (4) selecting a second progeny Pentas plant having a double flower or semi-double flower phenotype from Pentas plants obtained by artificial crossing of step (3), wherein steps (3) and (4) are conducted several times, and, optionally
   (3') artificially back-crossing the second progeny plant Pentas plant of step (4) with the second Pentas variety used in step (1) and
   (4') selecting a third progeny Pentas plant having a double flower or semi-double flower phenotype from Pentas plants obtained by artificial crossing of step (3'), wherein steps (3') and (4') are conducted several times.

\* \* \* \* \*